(12) United States Patent
Urick

(10) Patent No.: US 6,302,865 B1
(45) Date of Patent: Oct. 16, 2001

(54) INTRAVASCULAR GUIDEWIRE WITH PERFUSION LUMEN

(75) Inventor: Michael J. Urick, Rogers, MN (US)

(73) Assignee: SciMed Life Systems, Inc.

( * ) Notice: Subject to any disclaimer, the term of this patent is extended or adjusted under 35 U.S.C. 154(b) by 0 days.

(21) Appl. No.: 09/524,486

(22) Filed: Mar. 13, 2000

(51) Int. Cl.$^7$ ................................................. A61M 29/00
(52) U.S. Cl. ...................... 604/96.01; 604/104; 604/600; 604/3
(58) Field of Search ............. 604/96.01, 102.01–102.02, 604/264, 523, 528, 8, 99.01, 103.04, 103.08, 104; 600/434, 585, 1, 3

(56) References Cited

U.S. PATENT DOCUMENTS

| | | | |
|---|---|---|---|
| 2,546,761 | 3/1951 | Loftus | 128/1.2 |
| 2,862,108 | 11/1958 | Meilink | 250/106 |
| 2,955,208 | 10/1960 | Stevens | 250/108 |
| 3,060,924 | 10/1962 | Rush | 128/1.2 |
| 3,147,383 | 9/1964 | Prest | 250/108 |
| 3,324,847 | 6/1967 | Zoumboulis | 128/1.2 |
| 3,505,991 | 4/1970 | Hellerstein et al. | 128/1.1 |
| 3,643,096 | 2/1972 | Jeffries, Jr. et al. | 250/108 R |
| 3,669,093 | 6/1972 | Sauerwein et al. | 128/1.1 |
| 3,674,006 | 7/1972 | Holmer | 128/1.2 |
| 3,750,653 | 8/1973 | Simon | 128/1.2 |
| 3,811,426 | 5/1974 | Culver et al. | 128/1.2 |
| 3,861,380 | 1/1975 | Chassagne et al. | 128/1.2 |
| 3,866,050 | 2/1975 | Whitfield | 250/497 |
| 3,927,325 | 12/1975 | Hungate et al. | 250/435 |
| 4,096,862 | 6/1978 | DeLuca | 128/348 |
| 4,220,864 | 9/1980 | Sauerwein et al. | 250/497 |
| 4,225,790 | 9/1980 | Parsons, Jr. et al. | 250/497 |
| 4,244,357 | 1/1981 | Morrison | 128/1.2 |
| 4,281,252 | 7/1981 | Parson, Jr. et al. | 250/497 |
| 4,314,157 | 2/1982 | Gaines | 250/497 |
| 4,364,376 | 12/1982 | Bigham | 128/1.1 |
| 4,584,991 | 4/1986 | Tokita et al. | 128/1.1 |
| 4,588,395 | 5/1986 | Lemelson | 604/59 |
| 4,631,415 | 12/1986 | Sauerwen et al. | 250/497.1 |
| 4,702,228 | 10/1987 | Russell, Jr. et al. | 128/1.2 |
| 4,706,652 | 11/1987 | Horowitz | 128/1.2 |

(List continued on next page.)

FOREIGN PATENT DOCUMENTS

| | | |
|---|---|---|
| 2166915 A | 8/1996 | (CA) . |
| G 91 02 312 | 8/1992 | (DE) . |
| 195 26 680 A1 | 1/1997 | (DE) . |

(List continued on next page.)

OTHER PUBLICATIONS

Tjho–Heslinga et al., "Results of ruthenium irradiation of uveal melanoma", *Radiotherapy Oncology*, vol. 29, pp 33–38, 1993.

(List continued on next page.)

Primary Examiner—Sharon Kennedy
Assistant Examiner—Catherine Serke
(74) Attorney, Agent, or Firm—Crompton, Seager & Tufte, LLC

(57) ABSTRACT

A guidewire for use in combination with a balloon catheter having a guidewire lumen disposed distal of the balloon, wherein the guidewire defines a perfusion lumen extending from a point proximal of the balloon to a point distal of the balloon such that blood may perfuse across the balloon when inflated. The guidewire may be used in an intravascular balloon angioplasty system, an intravascular system for the administration of ionizing radiation utilizing a centering balloon catheter, or any other intravascular system utilizing a balloon catheter and a guidewire. The guidewire includes an elongate shaft wherein a distal a portion of the shaft defines the perfusion lumen. Alternatively, the perfusion lumen may be defined by a tubular member carried by the shaft. The tubular member may be fixed to the shaft or may be movable relative thereto. As a further alternative, the shaft may include an expandable portion which defines the perfusion lumen.

8 Claims, 2 Drawing Sheets

U.S. PATENT DOCUMENTS

| | | | |
|---|---|---|---|
| 4,763,642 | 8/1988 | Horowitz | 128/1.2 |
| 4,763,671 | 8/1988 | Goffinet | 128/786 |
| 4,782,834 | 11/1988 | Maguire et al. | 128/344 |
| 4,784,116 | 11/1988 | Russell, Jr. et al. | 128/1.2 |
| 4,815,449 | 3/1989 | Horowitz | 600/7 |
| 4,819,618 | 4/1989 | Liprie | 600/7 |
| 4,851,694 | 7/1989 | Rague et al. | 250/497.1 |
| 4,861,520 | 8/1989 | van't Hooft et al. | 252/644 |
| 4,881,937 | 11/1989 | van't Hooft et al. | 600/3 |
| 4,897,076 | 1/1990 | Puthawala etal. | 600/7 |
| 4,936,823 | 6/1990 | Colvin et al. | 600/7 |
| 4,963,128 | 10/1990 | Daniel et al. | 600/7 |
| 4,969,863 | 11/1990 | van't Hooft et al. | 600/3 |
| 4,976,266 | 12/1990 | Huffman etal. | 128/659 |
| 4,976,680 | 12/1990 | Hayman et al. | 600/7 |
| 4,976,690 | 12/1990 | Solar et al. | 604/96 |
| 5,030,194 | 7/1991 | Van't Hooft | 600/3 |
| 5,032,113 | 7/1991 | Burns | 604/96 |
| 5,059,166 | 10/1991 | Fischell et al. | 600/3 |
| 5,084,001 | 1/1992 | Van't Hooft et al. | 600/3 |
| 5,084,002 | 1/1992 | Liprie | 600/7 |
| 5,092,834 | 3/1992 | Bradshaw et al. | 600/7 |
| 5,103,395 | 4/1992 | Spako et al. | 364/413.26 |
| 5,106,360 | 4/1992 | Ishiwara et al. | 600/251 |
| 5,120,973 | 6/1992 | Rohe et al. | 250/497.1 |
| 5,139,473 | 8/1992 | Bradshaw et al. | 600/3 |
| 5,141,487 | 8/1992 | Liprie | 600/7 |
| 5,147,282 | 9/1992 | Kan | 600/1 |
| 5,163,896 | 11/1992 | Suthanthiran et al. | 600/8 |
| 5,176,617 | 1/1993 | Fischell et al. | 600/3 |
| 5,183,455 | 2/1993 | Hayman et al. | 600/7 |
| 5,199,939 | 4/1993 | Dake et al. | 600/3 |
| 5,213,561 | 5/1993 | Weinstein et al. | 600/7 |
| 5,252,159 | 10/1993 | Arney | 156/169 |
| 5,257,974 | 11/1993 | Cox | 604/96 |
| 5,267,958 | 12/1993 | Buchbinder et al. | 604/96 |
| 5,267,960 | 12/1993 | Hayman et al. | 604/106 |
| 5,282,781 | 2/1994 | Liprie | 600/3 |
| 5,302,168 | 4/1994 | Hess | 600/3 |
| 5,320,605 | 6/1994 | Sahota | 604/101 |
| 5,344,383 | 9/1994 | Liping | 600/3 |
| 5,354,257 | 10/1994 | Roubin et al. | 600/7 |
| 5,370,685 | 12/1994 | Stevens | 623/2 |
| 5,383,890 | 1/1995 | Miraki et al. | 606/194 |
| 5,391,139 | 2/1995 | Edmundson | 600/7 |
| 5,395,300 | 3/1995 | Liprie | 600/3 |
| 5,405,309 | 4/1995 | Carden, Jr. | 600/3 |
| 5,409,015 | 4/1995 | Palermo | 128/772 |
| 5,411,466 | 5/1995 | Hess | 600/3 |
| 5,413,557 | 5/1995 | Solar | 604/96 |
| 5,425,720 | 6/1995 | Rogalsky et al. | 604/198 |
| 5,429,582 | 7/1995 | Williams | 600/2 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,503,614 | 4/1996 | Liprie | 600/7 |
| 5,532,122 | 7/1996 | Drukier | 435/5 |
| 5,538,494 | 7/1996 | Matsuda | 600/1 |
| 5,540,659 | 7/1996 | Teirstein | 604/104 |
| 5,549,556 | 8/1996 | Ndondo-Lay et al. | 604/102 |
| 5,556,389 | 9/1996 | Liprie | 604/264 |
| 5,562,620 | 10/1996 | Klein et al. | 604/96 |
| 5,569,197 * | 10/1996 | Helmus et al. . | |
| 5,573,508 * | 11/1996 | Thornton . | |
| 5,575,749 | 11/1996 | Liprie | 600/3 |
| 5,575,771 | 11/1996 | Walinsky | 604/96 |
| 5,605,530 | 2/1997 | Fischell et al. | 600/3 |
| 5,611,767 | 3/1997 | Williams | 600/2 |
| 5,616,114 | 4/1997 | Thornton et al. | 600/3 |
| 5,618,266 | 4/1997 | Liprie | 604/21 |
| 5,624,372 | 4/1997 | Liprie | 600/3 |
| 5,643,171 | 7/1997 | Bradshaw et al. | 600/1 |
| 5,649,924 | 7/1997 | Everett et al. | 606/15 |
| 5,653,683 | 8/1997 | D'Andrea | 604/21 |
| 5,662,580 | 9/1997 | Bradshaw et al. | 600/3 |
| 5,674,177 | 10/1997 | Hehrlein et al. | 600/3 |
| 5,683,345 | 11/1997 | Waksmann et al. | 600/3 |
| 5,688,220 | 11/1997 | Verin et al. | 600/1 |
| 5,707,332 | 1/1998 | Weinberger | 600/3 |
| 5,713,828 | 2/1998 | Coniglione | 600/7 |
| 5,716,340 | 2/1998 | Schweich, Jr. et al. | 604/101 |
| 5,720,717 | 2/1998 | D'Andrea | 604/21 |
| 5,722,984 | 3/1998 | Fischell et al. | 600/198 |
| 5,728,042 | 3/1998 | Schwager | 600/3 |
| 5,730,698 | 3/1998 | Fischell et al. | 600/3 |
| 5,782,740 | 7/1998 | Schneiderman | 600/1 |
| 5,782,742 | 7/1998 | Crocker et al. | 600/3 |
| 5,795,286 | 8/1998 | Fischell et al. | 600/3 |
| 5,796,106 | 11/1999 | Verin et al. | 604/96 |
| 5,800,333 | 9/1998 | Liprie | 600/3 |
| 5,803,895 | 9/1998 | Kronholz et al. | 600/3 |
| 5,807,231 | 9/1998 | Liprie | 600/3 |
| 5,814,061 | 9/1998 | Osborne et al. | 606/194 |
| 5,816,259 | 10/1998 | Rose | 128/898 |
| 5,816,999 | 10/1998 | Bischoff et al. | 600/3 |
| 5,820,553 | 10/1998 | Hughes | 600/426 |
| 5,833,593 | 11/1998 | Liprie | 600/3 |
| 5,833,632 | 11/1998 | Jacobsen et al. | 600/585 |
| 5,840,008 | 11/1998 | Klein et al. | 600/3 |
| 5,840,009 | 11/1998 | Fischell et al. | 600/3 |
| 5,840,064 | 11/1998 | Liprie | 604/96 |
| 5,843,163 | 12/1998 | Wall | 623/1 |
| 5,851,171 | 12/1998 | Gasson | 600/3 |
| 5,851,172 | 12/1998 | Bueche et al. | 600/7 |
| 5,855,546 | 1/1999 | Hastings et al. | 600/3 |
| 5,857,956 | 1/1999 | Liprie et al. | 600/7 |
| 5,863,284 | 1/1999 | Klein | 600/3 |
| 5,863,285 | 1/1999 | Coletti | 600/3 |
| 5,865,720 | 2/1999 | Hastings et al. | 600/3 |
| 5,871,436 | 2/1999 | Eury | 600/3 |
| 5,871,437 | 2/1999 | Alt | 600/3 |
| 5,873,811 | 2/1999 | Wang et al. | 600/5 |
| 5,879,282 | 3/1999 | Fischell et al. | 600/3 |
| 5,882,290 | 3/1999 | Kume | 600/3 |
| 5,882,291 | 3/1999 | Bradshaw et al. | 600/3 |
| 5,882,336 | 3/1999 | Janacek | 604/96 |
| 5,891,091 | 4/1999 | Teirstein | 604/104 |
| 5,897,573 | 4/1999 | Rosenthal et al. | 606/224 |
| 5,899,882 * | 5/1999 | Waksman et al. . | |
| 5,906,573 | 5/1999 | Aretz | 600/3 |
| 5,910,101 | 6/1999 | Andrews et al. | 600/3 |
| 5,910,102 | 6/1999 | Hastings | 600/3 |
| 5,913,813 | 6/1999 | Williams et al. | 600/3 |
| 5,916,143 | 6/1999 | Apple et al. | 600/3 |
| 5,916,178 | 6/1999 | Noone et al. | 600/585 |
| 5,919,126 | 7/1999 | Armini | 600/3 |
| 5,921,958 * | 7/1999 | Resseman et al. . | |
| 5,924,973 | 7/1999 | Weinberger | 600/3 |
| 5,924,974 | 7/1999 | Loffler | 600/3 |
| 5,925,353 | 7/1999 | Mosseri | 424/178.1 |
| 5,938,582 | 8/1999 | Ciamacco, Jr. et al. | 600/3 |
| 5,947,889 | 9/1999 | Hehrlein | 600/3 |
| 5,947,924 | 9/1999 | Liprie | 604/96 |
| 5,947,958 | 9/1999 | Woodard et al. | 606/1.5 |
| 5,957,829 | 9/1999 | Thornton | 600/3 |
| 5,961,439 | 10/1999 | Chernomorsky et al. | 600/4 |
| 5,967,966 | 10/1999 | Kronholz et al. | 600/3 |
| 5,971,909 | 10/1999 | Bradshaw et al. | 600/3 |
| 5,976,106 | 11/1999 | Verin et al. | 604/96 |
| 5,997,462 | 12/1999 | Loffler | 600/6 |
| 5,997,463 | 12/1999 | Cutrer | 600/8 |

| | | | | | |
|---|---|---|---|---|---|
| 6,010,445 | 1/2000 | Armini et al. ............... 600/3 | WO 97/25102 | 7/1997 | (WO). |
| 6,013,019 | 1/2000 | Fischell et al. ............... 600/3 | WO 97/25103 | 7/1997 | (WO). |
| 6,013,020 | 1/2000 | Meloul et al. ............... 600/7 | WO 97/07740 | 9/1997 | (WO). |
| 6,019,718 | 2/2000 | Hektner ............... 600/3 | WO 97/40889 | 11/1997 | (WO). |
| 6,024,690 | 2/2000 | Lee et al. ............... 600/3 | WO 98/01183 | 1/1998 | (WO). |
| 6,030,333 | 2/2000 | Sioshansi et al. ............... 600/3 | WO 98/01184 | 1/1998 | (WO). |
| 6,033,357 | 3/2000 | Ciezki et al. ............... 600/3 | WO 98/01185 | 1/1998 | (WO). |
| 6,048,300 | 4/2000 | Thornton et al. ............... 600/7 | WO 98/01186 | 1/1998 | (WO). |
| 6,050,930 | 4/2000 | Teirstein ............... 600/3 | WO 98/11936 | 3/1998 | (WO). |
| 6,053,858 | 4/2000 | Buesche et al. ............... 600/3 | WO 98/16151 | 4/1998 | (WO). |
| 6,059,713 | 5/2000 | Urick et al. ............... 600/3 | WO 98/20035 | 5/1998 | (WO). |
| 6,059,752 | 5/2000 | Segal ............... 604/107 | WO 98/25674 | 6/1998 | (WO). |
| 6,059,812 | 5/2000 | Clerc et al. ............... 606/198 | WO 98/29049 | 7/1998 | (WO). |
| 6,066,083 | 5/2000 | Slater et al. ............... 600/8 | WO 98/30273 | 7/1998 | (WO). |
| | | | WO 98/34681 | 8/1998 | (WO). |

FOREIGN PATENT DOCUMENTS

| | | | | | |
|---|---|---|---|---|---|
| | | | WO 98/36788 | 8/1998 | (WO). |
| 197 58 234 | 12/1997 | (DE). | WO 98/36790 | 8/1998 | (WO). |
| 198 07 727 | 2/1998 | (DE). | WO 98/36796 | 8/1998 | (WO). |
| 198 25 563 | 6/1998 | (DE). | WO 98/39052 | 9/1998 | (WO). |
| 198 25 999 | 6/1998 | (DE). | WO 98/39062 | 9/1998 | (WO). |
| 198 26 000 | 6/1998 | (DE). | WO 98/39063 | 9/1998 | (WO). |
| 198 29 444 | 7/1998 | (DE). | WO 98/40032 | 9/1998 | (WO). |
| 198 29 447 | 7/1998 | (DE). | WO 98/46309 | 10/1998 | (WO). |
| 197 54 870 A1 | 8/1998 | (DE). | WO 98/55179 | 12/1998 | (WO). |
| 197 24 233 C1 | 12/1998 | (DE). | WO 98/57706 | 12/1998 | (WO). |
| 0 514 913 A2 | 11/1992 | (EP). | WO 99/01179 | 1/1999 | (WO). |
| 0 633 041 A1 | 1/1995 | (EP). | WO 99/02219 | 1/1999 | (WO). |
| 0 673 621 A1 | 9/1995 | (EP). | WO 99/04706 | 2/1999 | (WO). |
| 0 686 342 A1 | 12/1995 | (EP). | WO 99/04856 | 2/1999 | (WO). |
| 0 688 580 A1 | 12/1995 | (EP). | WO 99/10045 | 3/1999 | (WO). |
| 0 696 906 B1 | 2/1996 | (EP). | WO 99/21615 | 5/1999 | (WO). |
| 0 749 764 A1 | 12/1996 | (EP). | WO 99/21616 | 5/1999 | (WO). |
| 0 754 472 A2 | 1/1997 | (EP). | WO 99/22673 | 5/1999 | (WO). |
| 0 754 473 A2 | 1/1997 | (EP). | WO 99/22774 | 5/1999 | (WO). |
| 0 593 136 B1 | 3/1997 | (EP). | WO 99/22775 | 5/1999 | (WO). |
| 0 778 051 A1 | 6/1997 | (EP). | WO 99/22812 | 5/1999 | (WO). |
| 0 801 961 A2 | 10/1997 | (EP). | WO 99/22815 | 5/1999 | (WO). |
| 0 813 894 A2 | 12/1997 | (EP). | WO 99/24116 | 5/1999 | (WO). |
| 0810004 | 12/1997 | (EP). | WO 99/24117 | 5/1999 | (WO). |
| 0 826 395 A1 | 3/1998 | (EP). | WO 99/29354 | 6/1999 | (WO). |
| 0 629 380 B1 | 7/1998 | (EP). | WO 99/29370 | 6/1999 | (WO). |
| 0865803 | 9/1998 | (EP). | WO 99/29371 | 6/1999 | (WO). |
| 0904798 | 3/1999 | (EP). | WO 99/30779 | 6/1999 | (WO). |
| 0904799 | 3/1999 | (EP). | WO 99/34969 | 7/1999 | (WO). |
| 10071210 | 3/1998 | (JP). | WO 99/36121 | 7/1999 | (WO). |
| 2000014810 | 1/2000 | (JP). | WO 99/39628 | 8/1999 | (WO). |
| 2000024001 | 1/2000 | (JP). | WO 99/40962 | 8/1999 | (WO). |
| WO 0004953 | 2/2000 | (JP). | WO 99/40970 | 8/1999 | (WO). |
| WO 86/03124 | 6/1986 | (WO). | WO 99/40971 | 8/1999 | (WO). |
| WO 93/04735 | 3/1993 | (WO). | WO 99/40972 | 8/1999 | (WO). |
| WO 94/25106 | 11/1994 | (WO). | WO 99/40973 | 8/1999 | (WO). |
| WO 94/26205 | 11/1994 | (WO). | WO 99/40974 | 8/1999 | (WO). |
| WO 95/07732 | 3/1995 | (WO). | WO 99/42162 | 8/1999 | (WO). |
| WO 95/19807 | 7/1995 | (WO). | WO 99/42163 | 8/1999 | (WO). |
| WO 96/06654 | 3/1996 | (WO). | WO 99/42177 | 8/1999 | (WO). |
| WO 96/10436 | 4/1996 | (WO). | WO 99/44686 | 9/1999 | (WO). |
| WO 96/13303 | 5/1996 | (WO). | WO 99/44687 | 9/1999 | (WO). |
| WO 96/14898 | 5/1996 | (WO). | WO 99/49935 | 10/1999 | (WO). |
| WO 96/17654 | 6/1996 | (WO). | WO 99/56825 | 11/1999 | (WO). |
| WO 96/22121 | 7/1996 | (WO). | WO 99/56828 | 11/1999 | (WO). |
| WO 96/29943 | 10/1996 | (WO). | WO 99/61107 | 12/1999 | (WO). |
| WO 96/40352 | 12/1996 | (WO). | WO 99/62598 | 12/1999 | (WO). |
| WO 97/09937 | 3/1997 | (WO). | WO 99/66979 | 12/1999 | (WO). |
| WO 97/17029 | 5/1997 | (WO). | WO 0003292 | 1/2000 | (WO). |
| WO 97/18012 | 5/1997 | (WO). | WO 0004838 | 2/2000 | (WO). |
| WO 97/19706 | 6/1997 | (WO). | WO 0009212 | 2/2000 | (WO). |
| | | | WO 0029501 | 5/2000 | (WO). |

OTHER PUBLICATIONS

Lommatzsch et al., "Radiation effects of the optic nerve observed after brachytherapy of choroidal melanomas with 106Ru/106Rh plaques", *Graefe's Arch. Clin. Exp. Ophthalmology* vol. 232, pp. 482–487, 1994.

*Radiotherapy of Intraoculare and Orbital Tumors*, Springer–Verlak publishers, Berlin Heidelberg and New York , copyright 1993, pp. 23–30 and 363–367.

Fackelmann, "Harbinger of a Heart Attack", *Science News*, vol. 151, Jun. 14, 1997, pp. 374–375.

Raloff, "Nuclear Medicine Gets Friendlier—Experimental Therapies Seek to Poison Just the Disease", *Science News*, vol. 152, Jul. 19, 1997, pp. 40–41.

Sutherland, "Managing Cancer Through Synergy", *Administrative Radiology Journal*, Nov. 1996, pp. 21–27.

* cited by examiner

INTRAVASCULAR GUIDEWIRE WITH PERFUSION LUMEN

FIELD OF THE INVENTION

The present invention generally relates to intravascular medical devices. Specifically, the present invention relates to intravascular guidewires for use in combination with a balloon catheter.

BACKGROUND OF THE INVENTION

Angioplasty procedures have gained wide acceptance in recent years as an effective and efficient method for treating certain types of vascular disease. For example, angioplasty is widely used for treating clogged arteries in the heart. Angioplasty is also used for the treatment of a wide variety of vascular restrictions in various other parts of the vascular system.

Angioplasty is commonly performed utilizing a balloon dilatation catheter which dilates the clogged artery, thereby re-establishing acceptable blood flow through the artery. An angioplasty balloon catheter typically includes an elongate tubular shaft and an inflatable balloon disposed at the distal end of the shaft. In use, the balloon catheter is advanced through the vascular system until the balloon is disposed adjacent the restriction in the artery. The balloon catheter is typically advanced over a guidewire which facilitates navigation through the vascular system. Once the balloon is in the desired position, the balloon is inflated for approximately 30 seconds to two minutes after which the balloon is deflated and withdrawn if acceptable blood flow has been re-established.

An example of such a balloon dilatation catheter is disclosed in U.S. Pat. No. 5,921,958 to Ressemann et al. Ressemann et al. disclose a balloon dilatation catheter having a guidewire lumen disposed distal of the balloon. The guidewire extends adjacent the catheter shaft and balloon, and passes through the guidewire lumen. When the balloon is inflated, the guidewire is disposed between the exterior of the balloon and interior of the vessel wall. The balloon and the guidewire collectively occlude the vascular lumen when the balloon is inflated thereby preventing blood flow. By preventing the flow of blood across the treatment site, an ischemic reaction may occur if the flow of blood is occluded too long. It is desirable, therefore, to provide a path for the flow of blood across the inflated balloon. Although balloon catheter designs which incorporate a perfusion lumen are known, it is desirable to provide a perfusion path without increasing the design complexity of the balloon catheter.

In addition to balloon angioplasty, intravascular ionizing radiation therapy is being used increasingly to treat vascular disease. For example, the administration of ionizing radiation has been proposed as both a primary and a secondary therapy for treating vascular restrictions. Clinical studies have shown that ionizing radiation may be used to inhibit or prevent restenosis after percutaneous transluminal angioplasty.

A conventional procedure for the intravascular administration of ionizing radiation utilizes a centering catheter to maintain the radiation source wire radially centered in the vascular lumen. Such centering catheters commonly comprise balloon catheters such as the devices disclosed in European Patent Application No. 688 580 A1 to Verin et al. Verin et al disclose centering catheters utilizing a multi-lobed balloon. In FIG. 3 of Verin et al., a centering balloon catheter is illustrated incorporating a guidewire lumen distal of the balloon, similar to the arrangement disclosed by Ressemann et al. In use, the catheter of this embodiment may also result in the occlusion of blood flow across the treatment site when the balloon is inflated. Because treatment times for the administration of ionizing radiation are commonly longer than inflation times for balloon angioplasty, the likelihood of causing an ischemic reaction is greater with this particular procedure. Accordingly, it is desirable to provide a perfusion path across the treatment site while the balloon is inflated. It is particularly desirable to provide a perfusion path across the treatment site without increasing the design complexity of the centering catheter.

SUMMARY OF THE INVENTION

The present invention addresses the need to provide a perfusion path across the treatment site when using a balloon catheter with a guidewire lumen distal of the balloon. The present invention addresses this need without increasing the complexity of the balloon catheter by providing a guidewire which defines a perfusion lumen. The perfusion lumen defined by the guidewire extends from a point proximal of the balloon to a point distal of the balloon such that blood may perfuse across the balloon when inflated.

As used herein, the term guidewire refers to any medical device for use in combination with a balloon catheter wherein the device extends along side the balloon and includes a perfusion lumen such that blood may perfuse across the balloon when inflated. The guidewire of the present invention may be utilized in an intravascular balloon angioplasty system, an intravascular system for the administration of ionizing radiation utilizing a centering balloon catheter, or any other intravascular system utilizing a balloon catheter and a guidewire or similar device.

The guidewire of the present invention is particularly suitable for use in combination with a balloon catheter having a guidewire lumen distal of the balloon. Examples of such balloon catheters are disclosed in U.S. Pat. No. 5,921,958 to Ressemann et al. and European Patent Application No. 688 580 A1 to Verin et al., the entire disclosures of which are hereby incorporated by reference. With such balloon catheters, the guidewire of the present invention extends adjacent the shaft and balloon and passes through the guidewire lumen. The guidewire defines a perfusion lumen extending from a point proximal of the balloon to a point distal of the balloon such that blood may perfuse across the balloon when inflated.

The guidewire of the present invention may include an elongate shaft wherein a distal portion of the shaft defines the perfusion lumen. Alternatively, the perfusion lumen may be defined by a tubular member carried by the distal portion of the shaft. The tubular member may be fixed to the shaft or may be movable relative thereto. As a further alternative, the distal portion of the shaft may include an expandable portion which defines the perfusion lumen. For example, the expandable portion may comprise a tubular mesh that is radially expandable by longitudinal contraction.

BRIEF DESCRIPTION OF THE DRAWINGS

FIGS. 5A and 5B illustrate yet another alternative embodiment of the guidewire of the present invention incorporating an expandable portion, wherein FIG. 5A illustrates the expandable portion in the collapsed state and FIG. 5B illustrates the expandable portion in the expanded state.

Although each of the Figures only illustrate a distal portion of the intravascular system of the present invention, those skilled in the art will recognize the proximal portions of each individual device is conventional unless otherwise specified.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
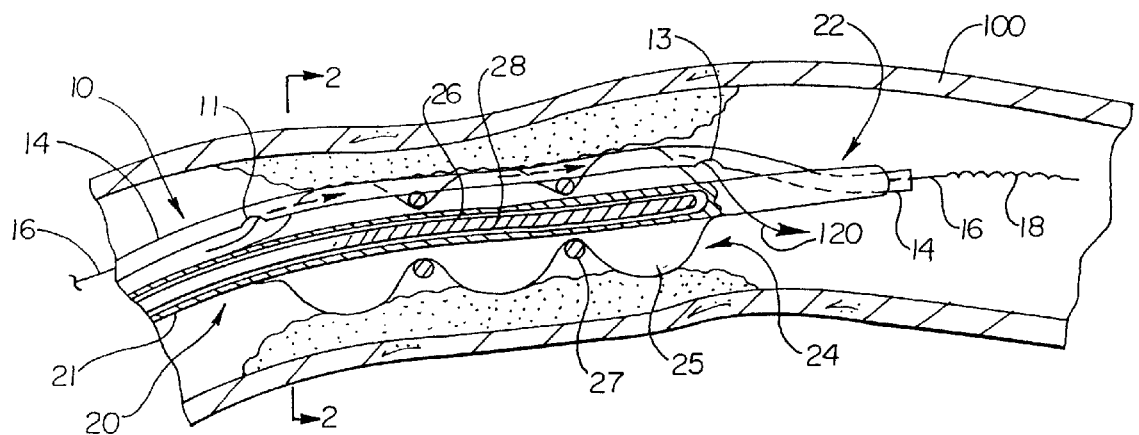
FIG. 1 illustrates a side view of a guidewire in accordance with an embodiment of the present invention used in combination with a centering balloon catheter (partially cross-sectioned) disposed in the vasculature.

Refer now to FIG. 1 which illustrates a partially cross-sectioned side view of a guidewire 10 in accordance with one embodiment of the present invention. Guidewire 10 is adapted for use in combination with an intravascular balloon catheter 20 having a guidewire lumen 22 disposed distally of the balloon 24. Balloon catheter 20 may comprise any of a wide variety of catheters that include a guidewire lumen disposed distally of the balloon. For example, catheter 20 may comprise the balloon catheter described in U.S. Pat. No. 5,921,958 to Ressemann et al. For purposes of illustration only, catheter 20 comprises the centering catheter shown in FIG. 3 of European Patent Application No. 688 580 A1 to Verin et al. In this particular embodiment, catheter 20 includes a centering balloon 24 disposed on the distal end of an elongate shaft 21. Centering balloon 24 includes a plurality of lobes 25 defined by intermediate waist portions 27. Centering balloon catheter 20 also includes a source lumen 26 adapted for insertion of a radioactive source wire 28.

Figure 2:
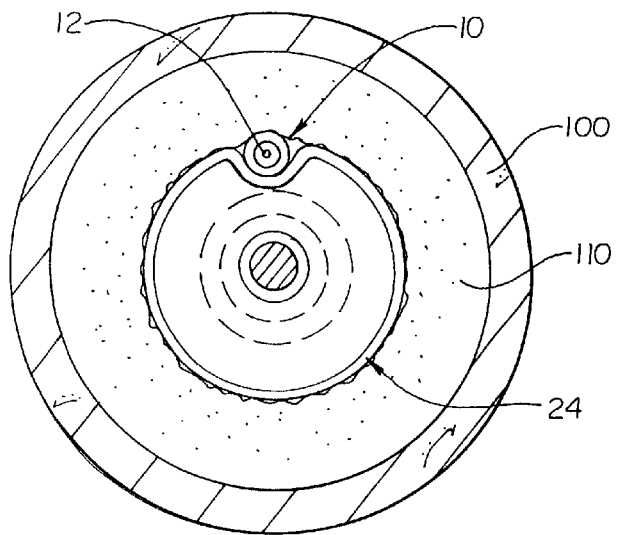
FIG. 2 illustrates a lateral cross-sectional view taken along line 2—2 in FIG. 1.

As seen in FIGS. 1 and 2, the guidewire 10 extends alongside the elongate shaft 21 and the inflatable balloon 24 and passes through the distal guidewire lumen 22. When the balloon 24 is inflated in the vasculature 100, particularly a vascular restriction 110, the guidewire 10 and the inflatable balloon 24 effectively occlude the flow of blood across the treatment site absent the provision of a perfusion lumen 12 defined by a distal portion of the guidewire 10. The perfusion lumen 12 extends from a proximal perfusion port 11 to a distal perfusion port 13. The proximal perfusion port 11 is positioned immediately proximal of the balloon 24 and the distal perfusion port 13 is disposed immediately distal of the balloon 24. In this position, the perfusion lumen 12 defines a fluid path by which blood may flow across the inflated balloon 24 as indicated by arrow 120.

The guidewire 10 includes a distal portion comprising a tubular member 14. Tubular member 14 defines the perfusion lumen 12 therein. The tubular member 14 extends along the distal portion of guidewire 10 but may optionally extend the full length of guidewire 10. The guidewire 10 may further include a core member 16 extending the full length of the guidewire 10 and terminating in a flexible tip 18. With the exception of the tubular member 14 defining the perfusion lumen 12, guidewire 10 may comprise conventional guidewire designs well known to those skilled in the art.

Alternatively, the distal portion of the guidewire 10, including or excluding the tubular member 14, may be formed of a material that is less attenuating (i.e., more transparent) to ionizing radiation as described in U.S. patent application Ser. No. 09/414,404, filed Oct. 7, 1999, entitled LOW ATTENUATION GUIDE WIRE FOR INTRAVASCULAR RADIATION DELIVERY, the entire disclosure of which is hereby incorporated by reference. Suitable materials that are less attenuating to ionizing radiation may be selected from the materials identified in Group A of Table 1. The proximal portion of the guidewire 10 may be formed of conventional materials such as those listed in Group B of Table 1. Similarly, the spring tip 18 may be formed of conventional materials such as those listed in Group C of Table 1. The materials identified in Group A are relatively less attenuating to ionizing radiation than the materials of Groups B and C. The materials identified in Group C are relatively more radiopaque than the materials of Groups A and B.

TABLE 1

| Group | Material | Atomic No. | Atomic Wt. | Density (g/cm³) |
|---|---|---|---|---|
| A | Polymer | 6.5* | 13.01* | 0.9–1.2** |
|   | Graphite | 6 | 12.01 | 2.3 |
|   | Aluminum | 13 | 26.98 | 2.70 |
|   | Glass | 14 | 28.09 | 2.3 |
| B | Titanium | 22 | 47.88 | 4.5 |
|   | Nickel Titanium | 25.3* | 53.29* | 6.7 |
|   | 304v SST | 25.9* | 54.50* | 7.9 |
| C | Tungsten | 74 | 183.84 | 19.3 |
|   | Platinum | 78 | 195.08 | 21.5 |

Notes:
*Estimated value
**Estimated range
Atomic weight based on carbon-12

The less attenuating materials identified in Group A of Table 1 may be used in pure form or may be combined with other materials. For example, the material comprising the region less attenuating to ionizing radiation may comprise a compound, an alloy, a composite, etc. An example of a composite is a polymer tube reinforced with carbon, aluminum, or glass fibers in the form of a coil, braid, or other suitable structure. Examples of polymers suitable for such a composite include polyethylene, polyurethane, polyimide, polyamide, nylon, etc.

The specific material or combination of materials selected from Group A is not critical as long as the desired region is less attenuating to ionizing radiation. Generally speaking, the materials listed in Group A are less attenuating ionizing radiation due to the relatively low atomic weight and density. Note that if a pure material is used, the atomic weight and density values may be obtained from Table 1. If a combination of materials (e.g., compound, an alloy, a composite, etc.) are utilized, the atomic weight and density values may be estimated by taking into account the ratio of each material used, in addition to the cross-sectional geometry and area occupied by the respective materials.

With this in mind, the region less attenuating to ionizing radiation may have an atomic number of less than 22, preferably less than 15, and more preferably less than 7. Similarly, the region less attenuating to ionizing radiation may have an atomic weight of less than 47, preferably less than 29, and most preferably less than 13. Also similarly, the region less attenuating to ionizing radiation may have a density of less than 4.5 g/cm³, preferably less than 2.3 g/cm³, and more preferably less than 2.0 g/cm³.

Generally, low energy gamma radiation is most sensitive to the atomic weight of the selected material, high energy gamma radiation is most sensitive to the density of the selected material, and beta radiation is most sensitive to both the atomic weight and density of the selected material. With this in mind, material selection may be based on the particular radioisotope to be used. If a low energy gamma ionizing radiation source is to be used, a low atomic weight material from Group A may be utilized. If a high energy gamma ionizing radiation source is to be used, a low density material selected from Group A may be used. If a beta ionizing radiation source is to be used, a low atomic weight and low density material may be selected from Group A.

Tubular member 14 preferably has an outside diameter of approximately 0.014 to 0.018 inches for coronary applications to approximate the nominal size of the guidewire 10. The wall thickness of the tubular member 14 is preferably minimized in order to obtain the maximum luminal diameter for the perfusion lumen 12. Perfusion lumen 12 should be sufficiently large to allow blood to flow freely therethrough, preferably at sufficient velocity to minimize the potential for stagnation and clotting.

The proximal perfusion port 11 is disposed at a point proximal of the balloon 24 and the distal perfusion port 13 is disposed at a point distal of the balloon 24 to facilitate perfusion across the inflated balloon 24. Accordingly, the distance between the proximal perfusion port 11 and the distal perfusion port 13 is a function of the length of the balloon 24, which is a function of the length of the treatment site. For example, if the balloon 24 has a length of approximately 2 cm, the perfusion ports 11 and 13 maybe separated by a distance of approximately 3 cm. Those skilled in the art will recognize that the size of the perfusion lumen and the distance between the proximal perfusion port 11 and the distal perfusion port 13 may be varied depending on the particular clinical application.

When the balloon 24 is inflated with the guidewire 10 adjacent thereto, an indentation may be formed along the length of the balloon 24 if the restriction 110 is relatively rigid and the balloon is inflated to a relatively low pressure. At higher pressures and/or with a relatively less rigid vascular restriction 110, such an indentation may not be formed. In this situation, the guidewire 10 may be pressed into the vascular restriction 110. This may or may not be desirable, depending on the particular clinical circumstances. If this effect is not desired, the balloon 24 may be molded to define an indentation extending the length thereof. The indentation should be sized to accommodate guidewire 10 such that guidewire 10 does not create a radial protrusion when the balloon 24 is inflated. Such an indentation should be in longitudinal alignment with the guidewire lumen 22 such that the guidewire 10 naturally rests within the indentation as the catheter is advanced and retracted along the guidewire 10.

In use, the guidewire 10 and the balloon catheter 20 are prepared for use by conventional techniques. After the guidewire 10 and the balloon catheter 20 are prepared for use, the guidewire 10 is loaded into the guidewire lumen 22 of the catheter 20 utilizing either a back-loading or front-loading technique. With the guidewire 10 disposed in the guidewire lumen 22, the guidewire 10 and the balloon catheter 20 are advanced through the vascular system. The guidewire 10 is navigated through the vascular system until the distal portion of the guidewire 10 is disposed across the treatment site, such as a vascular restriction 110. Radiopaque marker bands may be provided adjacent the proximal perfusion port 11 and the distal perfusion port 13 to facilitate radiographic positioning of the perfusion lumen 12 across the treatment site.

With the guidewire 10 in the desired position, the balloon catheter 20 is advanced until the balloon 24 is disposed across the treatment site. The balloon 24 is inflated to dilate the vascular restriction 110 and/or center the radioactive source 28. When inflated, the balloon 24 and the guidewire 10 effectively occlude the vascular lumen, absent the perfusion lumen 12. By providing perfusion lumen 12, blood is allowed to flow across the inflated balloon 24 as indicated by arrow 120 such that the vasculature distal of the treatment site receives sufficient oxygenated blood. After the restriction 110 has been sufficiently dilated or treated by ionizing radiation, the balloon 24 may be deflated, and the catheter 20 and the guidewire 10 may be subsequently removed.

Figure 3:
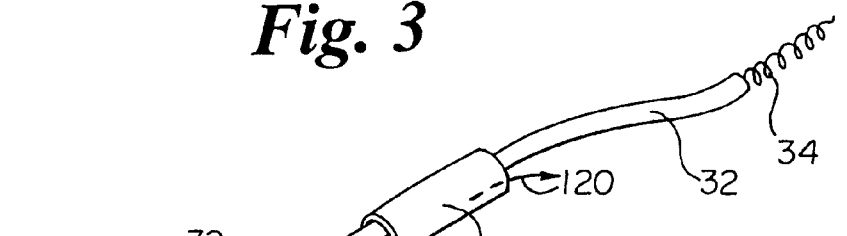
FIG. 3 illustrates an alternative embodiment of the guidewire of the present invention incorporating a fixed tubular member.

Refer now to FIG. 3 which illustrates guidewire 30 in accordance with an alternative embodiment of the present invention. Guidewire 30 is substantially the same in form, function and use as guidewire 10, except as described hereinafter. Guidewire 30 includes a conventional elongate shaft 32 and a conventional atraumatic distal tip 34. A tubular member 36 is disposed about or otherwise connected to the elongate shaft 32 adjacent a distal portion thereof. Tubular member 36 is fixedly attached to the elongate shaft 32 by suitable means such as adhesive or thermal bonding. Tubular member 36 has a sufficiently large inside diameter to define a perfusion lumen 38 through which blood may flow as indicated by arrow 120.

The perfusion lumen 38 has a length corresponding to the length between perfusion ports 11 and 13 as discussed with reference to guidewire 10. Guidewire 30 is used in substantially the same manner as guidewire 10, except tubular member 36 is positioned across the treatment site adjacent the balloon such that the proximal end of the tubular member 36 is disposed at a point proximal of the balloon 24 and the distal end of the tubular member 36 is disposed at a point distal of the balloon 24. Perfusion lumen 38 serves the same function as perfusion lumen 12 discussed with reference to guidewire 10.

Figure 4:
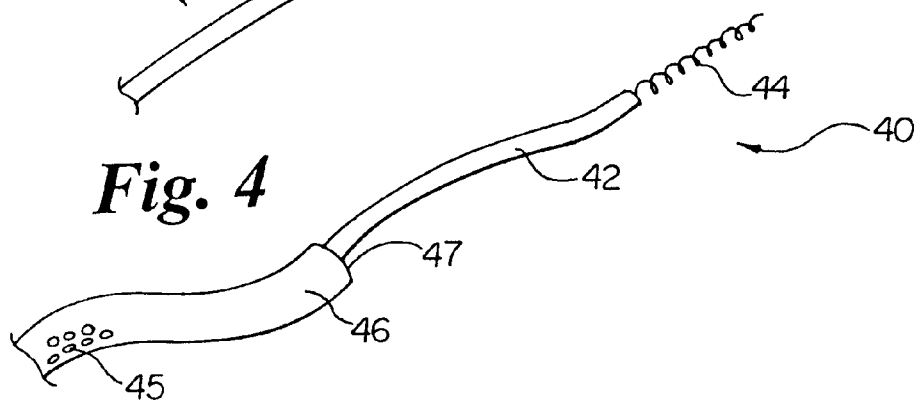
FIG. 4 illustrates a further alternative embodiment of the guidewire of the present invention incorporating a movable tubular member.

Refer now to FIG. 4 which illustrates guidewire 40 in accordance with yet another alternative embodiment of the present invention. Except as described hereinafter, guidewire 40 is substantially the same in form, function and use as guidewire 10. Guidewire 40 includes an elongate shaft 42 and a distally disposed atraumatic tip 44. A tubular member 46 is movably disposed about or otherwise moveably connected to the elongate shaft 42. The tubular member 46 preferably extends from the proximal end of the guidewire 40 to a distal portion on the elongate shaft 42. Tubular member 46 defines a perfusion lumen therein extending from a proximal perfusion port (or ports) 45 to a distal perfusion port 47. The distance between the proximal perfusion port 45 and the distal perfusion port 47 corresponds to the length between proximal perfusion port 11 and distal perfusion port 13 as discussed with reference to guidewire 10.

In this particular embodiment, the tubular member 46 is movable relative to the elongate shaft 42. This allows the tubular member 46 to be advanced over the guidewire 40 after the guidewire 40 and catheter 20 have been positioned across the treatment site. This also allows the tubular member 46 to be removed from the guidewire 40 to facilitate removal of catheter 20 while leaving guidewire 40 in place. In use, the tubular member 46 may be advanced over the elongate shaft 42 just prior to inflation. The proximal perfusion port 45 is positioned immediately proximal of the balloon and the distal perfusion port 47 is positioned immediately distal of the balloon 24. With this arrangement, a perfusion path is defined across the inflated balloon 24 extending from the proximal perfusion ports 45 through the interior of the tubular member 46 and out the distal perfusion port 47.

Figure 5A:
Figure 5B:
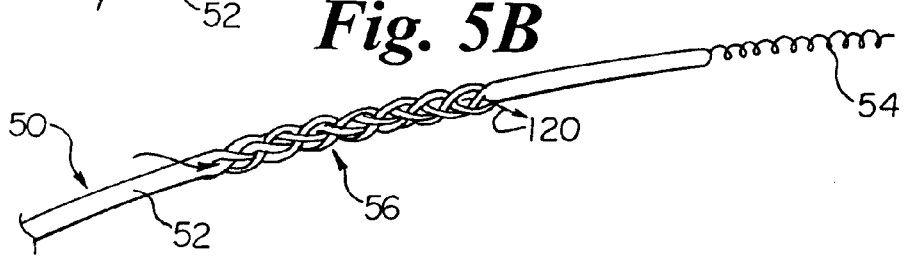

Refer now to FIGS. 5A and 5B which illustrate guidewire 50 in accordance with yet another embodiment of the present invention. Guidewire 50 is substantially the same in form, function and use as guidewire 10 except as described hereinafter. Guidewire 50 includes an elongate shaft 52 and a distally disposed atraumatic tip 54. An expandable portion 56 is disposed on the distal portion of the elongate shaft 52. FIG. 5A illustrates the expandable portion 56 in the collapsed state and FIG. 5B illustrates the expandable portion 56 in the expanded state. The expandable portion 56 preferably has a length in the expanded state corresponding to the length between the proximal perfusion port 11 and the distal perfusion port 13 as discussed with reference to guidewire 10. When the expandable portion 56 is in the expanded position as illustrated in FIG. 5B, a perfusion path is defined as indicated by arrow 120. The blood flows through the openings in the expandable portion 56.

Expandable portion 56 may be, for example, a tubular braid or similar structure that radially expands when longitudinally contracted. To facilitate longitudinal contraction, a pull wire may extend through the interior of the elongate shaft 52 and be connected to the distal end of the expandable portion 56. The proximal end of the expandable portion 56 is rigidly connected to the elongate shaft 52 such that is remains stationary when the pull wire is actuated. When the pull wire is actuated in the proximal direction, the distal end of the expandable portion 56 retracts thereby causing radial expansion of the braid. When the braid expands, blood flows between the individual wires or filaments defining the braid.

In practice, the guidewire 50 is navigated with the expandable portion 56 in the collapsed state as illustrated in FIG. 5A. When the catheter 20 is positioned with the balloon 24 disposed across the treatment site, the guidewire 50 is positioned such that the proximal end of the expandable portion 56 is disposed at a point proximal of the balloon 24 and the distal end of the expandable portion 56 is disposed at a point distal of the balloon 24. Just prior to inflation of the balloon 24, the expandable portion 56 is radially expanded to define a perfusion path therethrough as illustrated in FIG. 5B.

Those skilled in the art will recognize that the expandable portion 56 may be formed by other suitable structures such as an expandable helical coil, elastic tube or other similar structure. In addition, the expandable portion 56 may be actuated by longitudinal contraction as discussed above or by other suitable means such as torsional actuation, thermal actuation or other electrical actuation.

From the foregoing, it should be apparent to those skilled in the art that the present invention provides a guidewire 10/30/40/50 for use in combination with a balloon catheter wherein the guidewire 10/30/40/50 defines a perfusion lumen extending from a point proximal of the balloon to a point distal of the balloon. The present invention is particularly useful in combination with balloon catheters having a guidewire lumen disposed distal of the balloon. With such balloon catheters, the guidewire 10/30/40/50 of the present invention defines a perfusion path such that blood may perfuse across the balloon when inflated. By providing such a perfusion path, the likelihood of causing an ischemic reaction due to prolonged inflation is greatly reduced.

Those skilled in the art will recognize that the present invention may be manifested in a wide variety of forms other than the specific embodiments described and contemplated herein. Accordingly, departures in form and detail may be made without departing from the scope and spirit of the present invention as described in the appended claims.

What is claimed is:

1. An intravascular system for the administration of ionizing radiation, comprising:

a centering catheter including a shaft extending from a proximal end to a distal end, a centering balloon disposed adjacent the distal end of the shaft, a source lumen extending through the shaft, and a guidewire lumen extending through the shaft distal of the centering balloon;

an elongate radiation source disposed in the source lumen of the centering catheter, the radiation source including a radioactive distal portion; and a guidewire extending adjacent and exterior to the balloon and through the guidewire lumen, the guidewire having a perfusion lumen extending from a point proximal of the balloon to a point distal of the balloon such that blood may perfuse across the balloon when in an inflated state.

2. An intravascular system for the administration of ionizing radiation as in claim 1, wherein the guidewire includes a shaft, a portion of which defines the perfusion lumen.

3. An intravascular system for the administration of ionizing radiation as in claim 1, wherein the guidewire includes a shaft and wherein the perfusion lumen is defined by a tubular member carried by the guidewire shaft.

4. An intravascular system for the administration of ionizing radiation as in claim 3, wherein the tubular member is fixed to the guidewire shaft.

5. An intravascular system for the administration of ionizing radiation as in claim 3, wherein the tubular member is movable relative to the guidewire shaft.

6. An intravascular system for the administration of ionizing radiation as in claim 1, wherein the guidewire includes a shaft and wherein the guidewire shaft includes an expandable portion to define the perfusion lumen.

7. An intravascular system for the administration of ionizing radiation as in claim 6, wherein the expandable portion comprises a tubular braid.

8. An intravascular system for the administration of ionizing radiation as in claim 7, wherein the tubular braid is radially expandable by longitudinal contraction.

* * * * *